United States Patent
Auffret et al.

(10) Patent No.: US 7,323,572 B2
(45) Date of Patent: *Jan. 29, 2008

(54) PROCESS FOR CONTROLLING THE HYDRATE MIX OF A COMPOUND

(75) Inventors: Anthony David Auffret, Sandwich (GB); Michael Paul Fitzgerald, Sandwich (GB)

(73) Assignee: Pfizer Inc, New York, NY (US)

( * ) Notice: Subject to any disclaimer, the term of this patent is extended or adjusted under 35 U.S.C. 154(b) by 125 days.

This patent is subject to a terminal disclaimer.

(21) Appl. No.: 10/601,355

(22) Filed: Jun. 23, 2003

(65) Prior Publication Data

US 2004/0007689 A1   Jan. 15, 2004

Related U.S. Application Data

(60) Provisional application No. 60/399,491, filed on Jul. 29, 2002.

(30) Foreign Application Priority Data

Jul. 16, 2002  (GB) ................. 0216515.7

(51) Int. Cl.
*C07F 9/06* (2006.01)
*C07F 9/28* (2006.01)

(52) U.S. Cl. ..................................... 548/112
(58) Field of Classification Search ............... 252/70; 424/401, 405, 443; 548/112
See application file for complete search history.

(56) References Cited

U.S. PATENT DOCUMENTS 6,977,302 B2* 12/2005 Green et al. ............... 548/112

FOREIGN PATENT DOCUMENTS

WO        WO97/28169        8/1997

* cited by examiner

*Primary Examiner*—Rebecca Anderson
*Assistant Examiner*—Susannah Chung
(74) *Attorney, Agent, or Firm*—Steven T. Zelson; Jason G. Tebbutt

(57) ABSTRACT

This invention relates to a process for controlling the hydrate mix of a compound, or a composition comprising the compound, the compound being capable of forming a plurality of hydration forms of differing stability and also of dissolution to give a solution that, when frozen below the eutectic point, is a eutectic mixture. This invention further relates to disodium salt of fosfluconazole in the form of its trihydrate, its hexahydrate, or as a mixture of tri- and hexahydrates.

4 Claims, 1 Drawing Sheet

Figure 1:
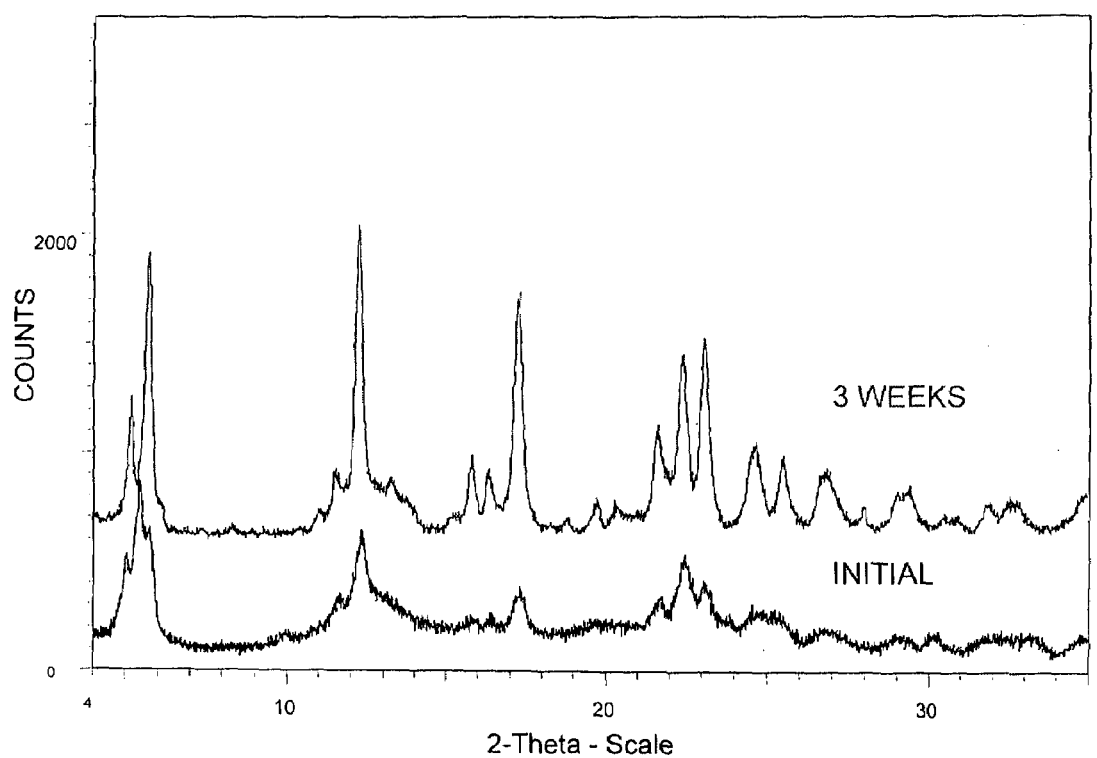

PXRD analyses of freeze dried DSFF: (a) shortly after drying (initial);and
(b) after storage for 3 weeks.

PROCESS FOR CONTROLLING THE HYDRATE MIX OF A COMPOUND

This application claims priority from U.S. Provisional Application Ser. No. 60/399,491 filed 29 Jul. 2002, which claims priority from United Kingdom Patent Application Number 0216515.7, filed 16 Jul. 2002, which are hereby incorporated by reference in their entireties.

FIELD OF THE INVENTION

This invention relates to a process for controlling the hydrate mix of a compound, or a composition comprising the compound, the compound being capable of forming a plurality of hydration forms of differing stability. More particularly, this invention relates to a process for controlling the hydrate mix of a compound, or a composition comprising the compound, the compound being capable of forming a plurality of hydration forms of differing stability and also of dissolution to give a solution that, when frozen below the eutectic point, is a eutectic mixture.

SUMMARY OF THE INVENTION

An example of a compound which exhibits a plurality of hydration forms is the disodium salt of fosfluconazole (hereinafter DSFF). DSFF is disclosed in WO97/28169 and has the following structure:

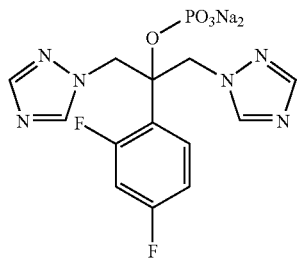

A number of hydration states of DSFF have now been found to exist and it is hypothesised that these are the dodecahydrate (33.4% w/w water), hexahydrate (20.1% w/w water), trihydrate (11.2% w/w water) and monohydrate (4.0% w/w water) forms. The anhydrous form of DSFF is believed to be amorphous. While the tri- and hexahydrate forms of DSFF are both chemically and thermally stable, it has been found that certain hydrate forms, such as the dodecahydrate, exhibit physical and/or chemical instability. While not wishing to be bound to any particular theory, it is believed that the eutectic form of DSFF is a dodecahydrate and it has been found that this dodecahydrate form is thermally unstable. Furthermore, it has been discovered that forms of DSFF which have a water content of from 4.0% w/w to 11.2% w/w are also chemically unstable. It is hypothesised that such a hydrate mix is a combination of tri- and monohydrate forms. Additionally, it has been found that samples of DSFF having a water content above the hexahydrate stoichiometry (20.1% w/w) collapse in a manner consistent with equilibration to the hexahydrate and water. Indeed, any composition comprising an unstable hydrate form, despite possibly containing stable forms, will decompose.

A stable hydration form of DSFF may be obtained by crystallisation from either acetonitrile/water or isopropanol/water mixtures. However, in order for the resulting product to be useful as a drug it must be sterile, but sterile recrystallisation is neither trivial nor economical.

Lyophilisation is a well known technique for the stabilisation of labile products which would otherwise be susceptible to biological or chemical degradation. The process has established itself as the standard method for the stabilization of many drug substances in the solid state to produce products of superior quality and stability.

It is well known in the art that for lyophilisation to take place a solution must be cooled to a temperature below which further cooling does not affect the phase composition, the so called eutectic temperature. Classical textbook models suggest that thermodynamic equilibrium eutectic freezing is universal. However, it is recognised in the art that it only occurs in the minority of frozen solutions and, actually, in the majority of cases a glass is formed. F. Franks, Cryo-Letters, 11, 93-110, 1990 teaches that the events taking place in a solution during the freezing process can seldom be predicted from equilibrium phase diagrams. In practice the solutes either incompletely precipitate or do not precipitate at all.

DSFF, however, is an example of a compound which is unusual, in that upon freezing it does conform to the classical models and precipitates from solution.

A typical freeze-drying process involves reducing the temperature of a compound, or a composition thereof, to below its "collapse" temperature. For a compound or composition thereof which undergoes crystallisation upon cooling, i.e. which behaves according to classical models, the collapse temperature will be the eutectic temperature. For a compound or a composition thereof which does not crystallise, or does so only partially, the collapse temperature will be the glass transition temperature of the freeze concentrate. Once the appropriate temperature conditions have been applied, the pressure in the apparatus is reduced from atmospheric pressure to from about 83.3 Pa to about 5.3 Pa, in order to sublime the ice from the frozen product. This is the primary drying phase. Ideally the temperature of the shelves in the apparatus should be kept below the collapse temperature of the compound or composition until all of the ice has been removed. However, it is common practice to increase the temperature in an attempt to speed up the process. In this situation, the shelf temperature must be kept to a level such that the heat coming into the system is balanced by the heat and mass transfer leaving the system, in order that the product never warms above its temperature of collapse. For the majority of compounds or compositions thereof, i.e. those which do not behave according to classical models, if the primary drying phase is extended beyond the time at which sublimation of the ice has been completed there is little effect. Once the primary drying phase has been completed, an amorphous compound will still typically contain a substantial amount of water (e.g. about 30% to about 50% by weight). Therefore, a secondary drying phase is undertaken to effect complete dehydration of the compound. The secondary drying process involves increasing the temperature of the shelves in the apparatus from below the collapse temperature to from about 25° C. to about 30° C.

However, it has been discovered that some compounds, and compositions thereof, more particularly those exhibiting a plurality of hydration forms of differing stability, may be deleteriously affected by being subjected to such a secondary drying phase. For example, when DSFF is subjected to a typical freeze-drying process a product is produced which has a water content of about 1.2% w/w, i.e. below its monohydrate stoichiometry (4.0% w/w water). This form of DSFF is chemically unstable and degrades. Furthermore, it has been discovered that forms of DSFF which have a water content of from 4.0% w/w to 11.2% w/w are also chemically unstable. It is hypothesised that such a hydrate mix is a combination of tri- and monohydrate forms. Additionally, it has been found that samples of DSFF having a water content above the hexahydrate stoichiometry (20.1% w/w) collapse in a manner consistent with equilibration to the hexahydrate and water.

The hydrate mix of a compound could, in principle, be controlled by a process which controls the Relative Humidity (RH) to which the compound is exposed. Such a process would comprise subjecting the compound or composition to a standard drying cycle in a freeze-drying apparatus followed by rehydration by providing a gas having an appropriately selected RH at a controlled temperature. However, in practice there would be a multitude of significant problems associated with such a process. Firstly, as discussed above, it is vital that compounds and compositions are prepared in sterile form when they are to be used for pharmaceutical purposes. This results in the significant practical problem of ensuring that the moist rehydration gas does not lead to corrosion or microbial contamination of the associated delivery system, which would severely impact on the economic viability of such a process. Furthermore, the rate of rehydration of the intermediate might not be sufficiently high to afford an economically viable process. In addition, it is possible that the compound or composition would be dried to the point that an unstable intermediate might be formed, which would mean that the end product of the process would be contaminated and therefore unacceptable for pharmaceutical use.

The apparent instability of compounds having a mixture of unstable and stable hydration states (e.g. the compound DSFF as a mixture of mono- and tri-hydrates) limits their potential utility as drugs owing to poor shelf life and there is a need in the art, therefore, for a process of producing a stable hydrate mix of such compounds. In particular there is a need in the art for a process for producing a mixture of the tri- and hexahydrate forms of DSFF.

Surprisingly, we have now found that a compound having a mixture of unstable and stable hydration states can be treated by the process of the current invention to provide a corresponding hydrate mix which is both chemically and thermally stable and can be prepared in a reproducibly facile and economically viable manner.

The present invention provides a process for the preparation of a stable hydrate mix of a compound, or a composition comprising the compound, the compound being capable of forming a plurality of hydration forms of differing stability and of dissolution to give a solution that, when frozen below the eutectic point, is a eutectic mixture, comprising:
a) providing a quantity of an aqueous mixture containing the compound or composition thereof in a suitable vessel in a freeze-drying apparatus;
b) reducing the temperature in the apparatus to bring about freezing and eutectic solidification;
c) reducing the pressure in the apparatus to below the saturation vapour pressure (SVP) of water over ice at the temperature of the ice;
d) maintaining the apparatus at a pressure below the SVP and, optionally, increasing the temperature in the apparatus to facilitate sublimation, until all of the ice has been sublimed;
e) maintaining the apparatus at the pressure and temperature conditions according to step d) until the desired water content has been obtained; and
f) either:
increasing the pressure in the apparatus to from about 60% to about 100% of atmospheric pressure (about 60.8 kPa to about 101.3 kPa) and subsequently adjusting the temperature in the apparatus to from about 5° C. to about 30° C.;
or
adjusting the temperature in the apparatus to from about 5° C. to about 30° C. and subsequently increasing the pressure in the apparatus to from about 60% to about 100% of atmospheric pressure (about 60.8 kPa to about 101.3 kPa).

Water in a solution will freeze at temperatures of from about −2° C. to about −15° C. Eutectic solidification is key to the invention; that is, all of the bulk, or freezable, water in the samples of compound contained within the freeze-drier apparatus must be frozen during step b). Unfortunately it is not possible to measure the exact point at which freezing is completed within the samples, nor is it possible to measure the exact point when the product crystallises. Preferably, therefore, the temperature selected in step b) is from about −10° C. to about −50° C., more preferably from about −20° C. to about −40° C. and most preferably the temperature is about −30° C., to ensure that freezing and crystallisation are completed.

The pressure selected in step c) should be below the SVP of water over ice at the temperature of the ice, i.e. at the compound or composition temperature. If a pressure above the SVP is used then there is a significant reduction in the driving force present to encourage the ice to sublime because the gas phase is saturated. As the pressure is lowered the driving force is increased, but if the pressure is too low the drying rate slows. This is because the heat transfer in the drier is mainly through the gas phase, even at reduced pressures. Therefore, at very low pressures the rate of heat input is decreased resulting in the reduction in the drying rate. Preferably, therefore, the pressure selected in step c) is from about 1 to about 250 Pa, more preferably from about 2 to about 125 Pa and most preferably about 4 to about 75 Pa (e.g. about 8 Pa).

Subliming water molecules remove energy, which results in a decrease in temperature of the ice within the compound or composition during the primary drying phase of the process. If the rate of sublimation of the ice from the sample is to be increased, the temperature must also be increased, as optionally indicated in step d) of the process. Whether the temperature of step d) represents an increase or not will, necessarily, depend on the temperature selected during step b), but typically the temperature selected in step d) is from about −50° C. to about 50° C., such as from about −25° C. to about 0° C., preferably about −15° C. A higher temperature than 50° C. must not be selected because there is a danger that the ice will not sublime but will pass into the liquid phase.

The apparatus is maintained at the conditions selected in step d) in order to remove the ice from the compound. However, as mentioned above, it has been discovered that certain compounds will continue to dehydrate, if maintained under reduced pressure conditions, once all of the ice has sublimed and this can have a deleterious affect on the quality of the resulting product. It is known in the art that a standard pressure rise test (PRT) will indicate the point of completion of the primary drying cycle (i.e. the sublimation stage). However, for compounds that continue to dehydrate once the sublimation has been completed, the rate at which water leaves the crystal structure may be sufficiently high that the PRT is passed significantly later than would be expected from sublimation of ice alone. Preferably the drying process is monitored at intervals of about one hour. Once the PRT has been passed the compounds may continue to dehydrate and an additional drying period may be required to give a product of the desired water content. This is the dehydration phase (e), which immediately follows the sublimation phase.

The duration of dehydration phase (e) depends upon the particular compound or composition, the vial diameter and fill volume and the type of drier used. The dehydration phase removes sufficient water from the compound to encourage formation of stable hydration forms and prevent the formation of unstable hydration forms. Should the dehydration phase be allowed to continue for longer than necessary, unstable hydration forms of the compound may be obtained, leading to instability. Typically the duration of the dehydration phase will be from 0 to 100 hours, such as 0 to 50 hours, preferably 6 to 30 hours, for example about 8, 12 or 28 hours.

With respect to step f), an increase in the pressure in the freeze-drying apparatus slows the dehydration phase sufficiently that the temperature may be increased to facilitate stoppering of the vials, thus allowing a stable hydrate mix to be achieved, although the order of these steps is not critical. Stoppering is conveniently carried out at 5° C. and 88% atmospheric pressure (i.e. 89.2 kPa).

This process may be applied to any compound, or composition, thereof, which exhibits multiple hydration forms of differing stability and which is also capable of dissolution to provide a solution which, when frozen, is a eutectic mixture. In particular this process may be applied to the production of a stable hydrate mix of DSFF. Preferably the final water content of the stable hydrate mix of DSFF is from about 11% to about 20% w/w, more preferably, from about 14% to about 17% w/w, most preferably from about 15% to about 16% w/w, such as about 15%.

DETAILED DESCRIPTION OF THE INVENTION

By way of illustration only, examples of the process conditions used to prepare a stable hydrate mix of DSFF will now be described. All examples were run in a Virtis Pilot Drier having an eight square foot shelf area and a condenser temperature of −56° C. 7.5 mTorr is equivalent to 1 Pa.

EXAMPLE 1

Vials (1320) having an internal diameter of 21.35 mm and a neck diameter of 20 mm were filled with 1.6 ml of a solution comprising 100.88 mg/ml fosfluconazole in NaOH/citric acid, adjusted to pH 9.05, thereby providing 179.8 mg of DSFF. The vials were placed in the drier and frozen at a shelf temperature of −30° C. for 3 hours. The shelf temperature was then increased to −15° C. and the pressure reduced to 8 Pa to facilitate sublimation. The PRT was passed at approximately 26 h after the start of ice sublimation and the samples dried for a further 12 hours before terminating the cycle by stoppering at 5° C. and 89.2 kPa pressure. The product was a stable hydrate mix with a mean water content of 11.7% w/w.

|  | Temperature/° C. | Pressure/mTorr | Time/hrs |
|---|---|---|---|
| Loading | 5 | | |
| Freezing | 5 | | 0.50 |
|  | −30 | | 1.47 |
|  | −30 | | 4.47 |
| Evacuation | −30 | 60 | 4.97 |
| Primary Drying | −30 | 60 | 5.13 |
|  | −15 | 60 | 5.55 |
|  | −15 | 60 | 7.55 |
|  | −15 | 60 | 17.55 |
|  | −15 | 60 | 22.55 |
|  | −15 | 60 | 25.55 |
|  | −15 | 60 | 26.55 |
|  | −15 | 60 | 27.55 |
|  | −15 | 60 | 28.55 |
|  | −15 | 60 | 29.55 |
|  | −15 | 60 | 30.55 |
| Dehydration Phase | −15 | 60 | 42.55 |

EXAMPLE 2

Vials (1173) having an internal diameter of 22.6 mm and a neck diameter of 20 mm were filled with 2.8 ml of a solution comprising 100.88 mg/ml fosfluconazole in NaOH/citric acid, adjusted to pH 9.05, thereby providing 314.6 mg of DSFF. The vials were placed in the drier and frozen at a shelf temperature of −30° C. for 3 hours. The shelf temperature was then increased to −15° C. and the pressure reduced to 8 Pa to facilitate sublimation. The PRT was passed at approximately 47 hours after the start of ice sublimation and the samples dried for a further 12 hours before terminating the cycle by stoppering at 5° C. and 89.2 kPa pressure. The product was a stable hydrate mix with a mean water content of 14.6% w/w.

|  | Temperature/° C. | Pressure/mTorr | Time/hrs |
|---|---|---|---|
| Loading | 5 | | |
| Freezing | 5 | | 0.50 |
|  | −30 | | 1.47 |
|  | −30 | | 4.47 |
| Evacuation | −30 | 60 | 4.97 |
| Primary Drying | −30 | 60 | 5.13 |
|  | −15 | 60 | 5.55 |
|  | −15 | 60 | 7.55 |
| PRT Intervals | −15 | 60 | 17.55 |
|  | −15 | 60 | 27.55 |
|  | −15 | 60 | 37.55 |
|  | −15 | 60 | 47.55 |
|  | −15 | 60 | 49.55 |
|  | −15 | 60 | 50.55 |
|  | −15 | 60 | 51.55 |
| Dehydration Phase | −15 | 60 | 63.55 |

EXAMPLE 3

Vials (1173) having an internal diameter of 22.6 mm and a neck diameter of 20 mm were filled with 5.4 ml of a solution comprising 100.88 mg/ml fosfluconazole in NaOH/citric acid, adjusted to pH 9.05, thereby providing 606.8 mg of DSFF. The shelf temperature was then increased to −15° C. and the pressure reduced to 8 Pa to facilitate sublimation. The PRT was passed at approximately 96 h after the start of ice sublimation and the samples dried for a further 12 hours before terminating the cycle by stoppering at 5° C. and 89.2 kPa pressure. The product was a stable hydrate mix with a mean water content of 16.9% w/w.

| | Temperature/° C. | Pressure/mTorr | Time/hrs |
|---|---|---|---|
| Loading | 5 | | |
| Freezing | 5 | | 0.5 |
| | −30 | | 1.47 |
| | −30 | | 4.47 |
| Evacuation | −30 | 60 | 4.97 |
| Primary Drying | −30 | 60 | 5.13 |
| | −15 | 60 | 5.55 |
| | −15 | 60 | 7.55 |
| | −15 | 60 | 17.55 |
| | −15 | 60 | 27.55 |
| | −15 | 60 | 37.55 |
| | −15 | 60 | 47.55 |
| | −15 | 60 | 57.55 |
| | −15 | 60 | 67.55 |
| | −15 | 60 | 77.55 |
| | −15 | 60 | 87.55 |
| | −15 | 60 | 88.55 |
| | −15 | 60 | 89.55 |
| | −15 | 60 | 90.55 |
| | −15 | 60 | 91.55 |
| | −15 | 60 | 92.55 |
| | −15 | 60 | 93.55 |
| | −15 | 60 | 94.55 |
| | −15 | 60 | 95.55 |
| | −15 | 60 | 96.55 |
| | −15 | 60 | 97.55 |
| | −15 | 60 | 98.55 |
| | −15 | 60 | 99.55 |
| | −15 | 60 | 100.55 |
| Dehydration Phase | −15 | 60 | 112.55 |

In the Examples that follow, Powder X-ray diffraction patterns were determined using a Bruker-AXS Ltd D8 Advance powder X-ray diffractometer fitted with a theta-theta goniometer, Gobel mirror and a position-sensitive detector. The samples were prepared for analysis by placing the powder on to silicon wafer specimen mounts. Each specimen was irradiated with copper K-alpha$_1$ X-rays (wavelength=1.5406 Å) with the X-ray tube operated at 40 kV/40 mA. The analyses were performed with the goniometer running in continuous mode set for a 0.3 second count per 0.014° step over a two theta range of 4° to 35° 2Θ.

EXAMPLE 4

Vials (582), 10 ml Type 1 Clear glass with a 20 mm neck diameter were filled with 2.9 ml of a solution comprising 100.88 mg/ml fosfluconazole in NaOH/citric acid adjusted to pH 9.0, thereby providing 325.8 mg of DSFF. The vials were placed in the drier and frozen at a shelf temperature of −30° C. for 3.5 hours. The shelf temperature was then increase to −15° C. and the pressure reduced to 6 Pa to facilitate sublimation. After 58.3 hours of sublimation the cycle was terminated by stoppering at 5° C. and 96 kPa pressure.

| | Temperature/° C. | Pressure/mTorr | Time/hrs |
|---|---|---|---|
| Loading | 5 | | |
| Freezing | −30 | | 3.00 |
| | −30 | | 3.50 |
| Evacuation | −30 | 45 | 4.25 |
| Primary Drying/Dehydration | −30 | 45 | 4.50 |
| | −30 | 45 | 5.00 |
| | −15 | 45 | 50.00 |
| | −15 | 45 | 63.30 |

The product from the above process is found to have a water content consistent with a stoichiometry between the hexa- and trihydrate forms. Powder X-ray Diffraction (PXRD) analysis of the product suggests that immediately after processing it has little long-range order, but that it does, however, have a high degree of crystallinity, see FIG. 1. The crystallinity of the sample is seen to increase after a storage period of several weeks. The PXRD pattern of the sample can be interpreted as a mixture of tri- and hexahydrate forms of DSFF. This mixture is both chemically and thermally stable. The PXRD data corresponding to FIG. 1 follow:

| PXRD "INITIAL" | | | | | |
|---|---|---|---|---|---|
| 2-Theta° | Intensity % | 2-Theta° | Intensity % | 2-Theta° | Intensity % |
| 5.011 | 64.3 | 15.826 | 32 | 26.768 | 29.1 |
| 5.412 | 100 | 17.336 | 45.8 | 29.115 | 24.1 |
| 5.7 | 75.3 | 21.63 | 41.5 | 30.194 | 24.1 |
| 9.959 | 25.7 | 22.456 | 64.1 | 31.874 | 24.1 |
| 11.005 | 32 | 23.089 | 50.2 | 33.175 | 24.1 |
| 11.545 | 42.3 | 24.802 | 37.4 | 34.824 | 24.9 |
| 12.33 | 75.2 | | | | |

| PXRD "3 WEEKS" | | | | | |
|---|---|---|---|---|---|
| 2-Theta° | Intensity % | 2-Theta° | Intensity % | 2-Theta° | Intensity % |
| 5.062 | 47.9 | 17.186 | 77.5 | 26.737 | 25.1 |
| 5.631 | 91.8 | 18.776 | 11.3 | 27.91 | 13.9 |
| 6.026 | 17.3 | 19.664 | 16.5 | 28.988 | 18.6 |
| 10.91 | 13.4 | 20.235 | 14.7 | 29.305 | 20.3 |
| 11.449 | 25.5 | 21.545 | 38.5 | 30.733 | 10.8 |
| 12.164 | 100 | 22.317 | 59.3 | 31.811 | 15.2 |
| 13.162 | 24.2 | 23 | 66 | 32.604 | 15.2 |
| 15.711 | 29 | 24.56 | 32.8 | 34.792 | 19.5 |
| 16.27 | 25.5 | 25.415 | 28.5 | | |

Not wishing to be bound by any particular theory, it is thought that a significant change in structure, as might on first inspection be implied by the PXRD analysis, does not actually occur; the molecules within the sample are thought to be in a crystalline array. Rather, removal of water molecules during the drying process results in disordered distribution of those water molecules remaining in the sample and, it is believed, it is this disordered distribution of water molecules which disrupts the repetitive long range repeating order (FIG. 1—INITIAL). Over time the system equilibrates such that the water molecules redistribute and their resulting distribution no longer disrupts the repetitive long range repeating order (FIG. 1—3 WEEKS).

EXAMPLE 5

DSFF Trihydrate (a) DSFF Hexahydrate

Fosfluconazole (40 g) was slurried in water (120 ml) and sodium hydroxide (7-8 ml of a 47% solution, circa 4.9-5.6 g NaOH) added stepwise, under nitrogen until a solution formed. The temperature was maintained between ambient and 30° C. The solution was filtered. Sodium hydroxide (42 ml of a 47% solution, circa 29.6 g NaOH) was added to the filtrate until precipitation occurred. The mixture was granulated for 4 hours, filtered under vacuum and dried in vacuo at 50° C. to afford the title compound (23.79 g). PXRD:

| 2-Theta° | Intensity % | 2-Theta° | Intensity % | 2-Theta° | Intensity % |
|---|---|---|---|---|---|
| 4.938 | 8.3 | 19.756 | 5.4 | 28.6 | 17.6 |
| 9.969 | 7 | 20.14 | 30.8 | 28.722 | 19.8 |
| 11.038 | 10.1 | 20.709 | 11.6 | 29.092 | 29.5 |
| 12.114 | 12.9 | 21.625 | 44.4 | 29.986 | 35.7 |
| 12.383 | 9 | 21.924 | 30.9 | 30.45 | 15.7 |
| 13.0 | 7.2 | 22.269 | 84.6 | 30.636 | 18.3 |
| 13.226 | 17.1 | 22.465 | 100 | 31.503 | 29.5 |
| 14.608 | 3.6 | 23.113 | 20.6 | 31.91 | 32.7 |
| 15.035 | 23 | 23.604 | 48.4 | 31.997 | 30 |
| 15.579 | 28.3 | 24.536 | 25.3 | 32.27 | 32.2 |
| 16.582 | 13.4 | 24.777 | 33.8 | 33.127 | 58.1 |
| 16.978 | 27.4 | 25.011 | 35.2 | 33.678 | 13 |
| 17.163 | 9.4 | 25.263 | 67 | 34.302 | 25.9 |
| 17.477 | 22.7 | 26.549 | 20.2 | 34.693 | 27.8 |
| 18.307 | 13.6 | 27.19 | 24.5 | 34.976 | 30.3 |
| 19.232 | 23.6 | 28.416 | 22.3 | | |

(b) DSFF Trihydrate

The title compound was prepared in situ, from circa 5 mg of the DSFF hexahydrate of Example 5(a), by heating at 60° C. on the PXRD stage. PXRD:

| 2-Theta° | Intensity % | 2-Theta° | Intensity % | 2-Theta° | Intensity % |
|---|---|---|---|---|---|
| 5.668 | 49.6 | 17.226 | 93.8 | 26.742 | 31.4 |
| 11.505 | 23 | 19.563 | 14.9 | 27.815 | 9.8 |
| 12.183 | 100 | 20.298 | 11.4 | 28.988 | 23.9 |
| 12.654 | 38.4 | 20.806 | 11.1 | 29.21 | 26 |
| 13.181 | 21.4 | 21.561 | 41.4 | 30.194 | 15.6 |
| 13.717 | 15.4 | 22.328 | 70.8 | 30.701 | 11.7 |
| 14.499 | 9.5 | 22.986 | 69.5 | 31.771 | 23.8 |
| 15.255 | 7.4 | 24.518 | 41.9 | 32.636 | 21.2 |
| 15.74 | 32.5 | 25.443 | 34.2 | 34.887 | 28.1 |
| 16.27 | 21.8 | | | | |

EXAMPLE 6

DSFF Hexahydrate

Fosfluconazole (26 mmols, 10 g) was dissolved in a solution of sodium hydroxide (54 mmols, 2.179 final volume circa 20 ml) and heated to 70° C. Isopropyl alcohol (108 ml), was added, in the temperature range 60-72° C., and the cloudy solution left to cool to provide the title compound as a slurry of crystals. A single crystal of DSFF hexahydrate was removed therefrom and mounted on a Bruker Diffractometer. The PXRD of Example 6 was consistent with that for Example 5(a).

The invention claimed is:

1. The disodium salt of fosfluconazole in the form of its trihydrate, its hexahydrate, or as a mixture of tri- and hexahydrates, wherein the trihydrate has a water content of about 11% w/w and the hexahydrate has a water content of about 20% w/w.

2. A hydrate mix of fosfluconazole disodium salt, wherein the water content of said mix is from about 11% w/w to about 20% w/w.

3. The hydrate mix according to claim 2, wherein the water content of said mix is from about 14% w/w to about 17% w/w.

4. The hydrate mix according to claim 3, wherein the water content of said mix is about 15% w/w.

* * * * *